United States Patent [19]
Mayerhoefer et al.

[11] 3,954,770
[45] May 4, 1976

[54] N,N'-(POLYBROMOPHENOXYCARBONYL)-PIPERAZINES

[75] Inventors: Horst Mayerhoefer, Oberwil; Wolfgang Mueller, Neuallschwil; Urs Sollberger, Fullinsdorf; Anton Voykowitsch, Binningen, all of Switzerland

[73] Assignee: Sandoz Ltd., Basel, Switzerland

[22] Filed: Oct. 31, 1974

[21] Appl. No.: 519,402

[30] Foreign Application Priority Data
Nov. 6, 1973    Switzerland............ 15597/73
Mar. 1, 1974    Switzerland............ 2934/74

[52] U.S. Cl. ............ 260/268 C; 260/45.8 N; 260/471 C; 260/479 C
[51] Int. Cl.² ............................. C07D 295/20
[58] Field of Search ................... 260/268 C

[56] References Cited
FOREIGN PATENTS OR APPLICATIONS
1,617,982   8/1970   Germany
1,668,085   4/1971   Germany OTHER PUBLICATIONS
D. E. Rivett et al., Chemical Abstracts, Vol. 65, 1966, pp. 3872–3874.

*Primary Examiner*—Raymond V. Rush
*Assistant Examiner*—Jose Tovar
*Attorney, Agent, or Firm*—Gerald D. Sharkin; Richard E. Vila; Joseph J. Borovian

[57] ABSTRACT

Flame retarding compounds of formula,

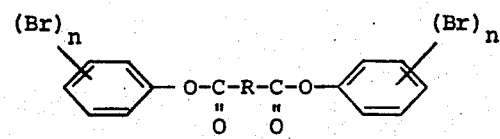

in which
each $n$, independently, is an integer 2 to 5, and
$R$ is a divalent radical of formula

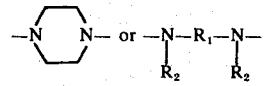

wherein
$R_1$ is alkylene or arylene and each
$R_2$, independently, is alkyl or phenyl,
for incorporation in organic materials such as plastics materials.

4 Claims, No Drawings

N,N'-(POLYBROMOPHENOXYCARBONYL)PIPERAZINES

The present invention relates to flame retarding compounds and their use in flameproofing organic materials. More particularly, the flame retarding compounds of the present invention are diaryl esters of dicarboxylic acids.

Accordingly, there are provided flame retarding compounds of formula I,

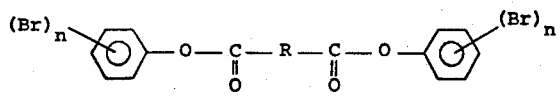   I in which
  each $n$, independently, is an integer 2 to 5,
and
  R is a divalent radical of formula

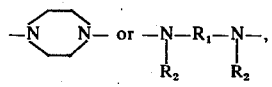

wherein
  $R_1$ is a $C_{2-6}$ alkylene radical, a m- or p-phenylene radical which is unsubstituted or substituted by up to 4 halogen atoms, or p,p'-diphenylene,
and
  each $R_2$, independently, is a $C_{1-4}$ alkyl radical or phenyl.

In the above definition, "halogen" indicates chlorine or bromine. Within the scope of "alkyl" is included straight chain, branched chain, primary and secondary alkyl containing up to 4 carbon atoms. Examples of alkylene radicals are straight chain $C_{2-6}$ alkylene radicals, of which ethylene and 1,3-propylene are members.

Of the significances for R, the piperazinyl radical is the preferred significance. When R has the significance $-N(R_2)-R_1-N(R_2)-$, $R_1$ is preferably a $C_{2-6}$ alkylene or an optionally halogen-substituted m- or p-phenylene radical, and, independently of $R_1$, $R_2$ is preferably a $C_{1-4}$ alkyl radical. Furthermore, when $R_1$ is an alkylene radical, this is preferably ethylene, when it is an optionally halogen-substituted m- or p-phenylene radical, unsubstituted p-phenylene is preferred, and when $R_2$ is an alkyl radical, this is preferably methyl or ethyl. Preferably the compounds of formula I are symmetrical, i.e. with respect to $n$ and the positions of the bromine atoms on the benzene nuclei, and, in the cases where R has the significance $-N(R_2)-R_1-N(R_2)-$, the values of the two $R_2$'s are identical.

In accordance with the above indications of preferred significances, a preferred group of flame retarding compounds of formula I are those of formula Ia,

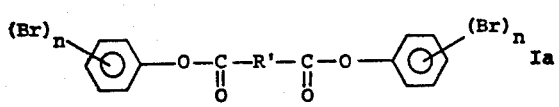   Ia in which $n$ is as defined above,
and
R' is a divalent radical of formula

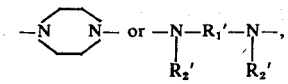

wherein
  $R_1'$ is a $C_{2-6}$ alkylene radical or p-phenylene,
and
  each $R_2'$, independently, is methyl or ethyl.

A preferred group of flame-retarding compounds of formula Ia are those of formula Ib,

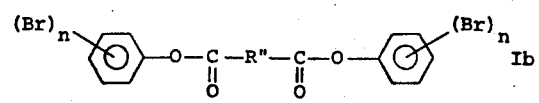   Ib in which
  $n$ is as defined above,
and
  R'' is a divalent radical of formula

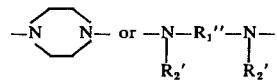

wherein
  $R_1''0$ is ethylene or p-phenylene, and $R_2'$ is as defined above.

A preferred group of flame retarding compounds of formula Ib are those of formula Ic,

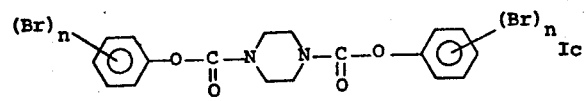   Ic in which
  $n$ is as defined above.

The invention further provides a process for the production of a compound of formula I, which comprises reacting a compound or a mixture of compounds of formula II,

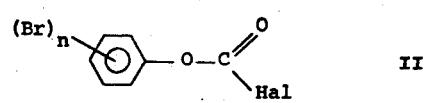   II in which
  $n$ is as defined above, and Hal is chlorine or bromine, with a compound of formula III,

H—R—H   III in which
  R is as defined above.

Examples of compounds of formula II useable in the process of the present invention are the 2,4-dibromophenyl, 2,6-dibromophenyl, 2,4,6-tribromophenyl, 2,4,5-tribromophenyl, 2,3,4,5-tetrabromophenyl, 2,3,4,6-tetrabromophenyl and pentabromophenyl esters of chlorocarbonic acid. Amongst the compounds of formula III useable in the process are 1,4-bis (methylamino) benzene, 1,3-bis (ethylamino) benzene, 4,4'-bis (methylamino) diphenyl, 1,2-bis (methylamino) ethane, 1,2-bis (ethylamino)ethane and 1,6-bis (methylamino) hexane.

The process of the present invention is generally carried out in a reaction-inert organic solvent, e.g. benzene, toluene, hexane, a petroleum fraction or dioxan. Preferably, the reagents are reacted within the temperature range 10° to 30°C, preferably in the presence of a base, of which tertiary amines such as triethylamine and pyridine, bicarbonates such as sodium bicarbonate, sodium carbonate and sodium hydroxide are suitable examples. The reaction is preferably completed at room temperature or at an elevated temperature, for example at the boiling point of the solvent.

The present invention further provides a method of reducing the inflammability of an organic material which comprises incorporating therein a compound of formula I, as hereinbefore defined. Particularly susceptible to the method of the present invention are plastics materials such as polymeric organic materials. Examples of polymeric organic materials suitably treated according to the method are polyolefins, e.g. polyethylene and polypropylene, polyesters, polyacrylic esters, e.g. polymethyl methacrylates, polyphenylene oxides, polyurethanes, polystyrene, polycarbonate, acrylonitrile-butadienestyrene (ABS) terpolymers, polyamides and especially nylon, polypropylene oxide, polyacrylonitrile and copolymers of the aforementioned polymers. The compounds of the invention are especially suitable for reducing the inflammability of polypropylene, polyethylene, polyesters, polyamide, polyurethanes, polyacrylonitrile, acrylonitrile-butadiene-styrene (ABS) terpolymers, acrylic ester-styrene-acrylonitrile terpolymers, styrene-acrylonitrile copolymers and styrene-butadiene copolymers. A preferred polyester is polyethylene terephthalate.

Any of the known methods may be used to incorporate the flame retarding compounds of the present invention in the organic materials to be treaed. For example, the flame retarding compound may be mixed with the organic material, e.g. in particulate form, in a kneader or other suitable mixing device, to obtain the desired incorporation of the compound in the organic material. The latter may then be formed into the desired final shape, e.g. by extrusion into the form of, inter alia, films and fibres, or by injection moulding. In another method of incorporation, particularly suited to reducing the inflammability of polymers or copolymers, e.g. polyurethanes, the compound is mixed with the appropriate monomers or prepolymers before polymerisation or copolymerisation is effected. Subsequently, the treated materials may be converted into such forms as injection moulded articles, spinning masses, extruded articles, split fibres and textile fibres.

The compounds according to the invention are notable for their high thermostability properties, and are therefore especially suitable for incorporation into polymer melts, e.g. polypropylene or polyester at temperatures up to 300°C. At a subsequent stage in the processing of the organic material, it is formed into final shape, e.g. by extrusion into such forms as films and fibres, or by injection moulding.

The amount of flame retarding compound of formula I suitably incorporated in the organic material for imparting satisfactory flame retardant properties thereto will naturally depend, inter alia, on the particular compound used and the nature of the organic material to be treated, and so will fall within a wide range. In general, however, satisfactory results are obtained when the amount of compound of formula I employed is in the range 1–40%, preferably 2–20%, and even more preferably, 3–10% of the weight of the organic material to be treated.

The present invention further provides an organic material having incorporated therein as a flame retarding agent a compound of formula I, as hereinbefore defined.

In the following Examples the parts and percentages are by weight and the temperatures are in degrees Centigrade. The indicated structures of the compounds were determined by microanalysis and infra-red spectroscopy.

EXAMPLE 1

A solution of 6.5 parts of piperazine in 200 parts of absolute dioxan is added at 10°C over the course of 3 minutes to a solution of 29.5 parts of chlorocarbonic acid-2,4,6-tribromophenyl ester and 200 parts of absolute dioxan. The reaction mixture is allowed to react at room temperature for 3 hours and a white solid is obtained. 15.2 Parts of triethylamine, dissolved in 50 parts of dioxane, are then added dropwise over the course of 5 minutes. The mixture is kept at 40° for 2 hours, subsequently cooled to 10°C and 29.5 parts of chlorocarbonic acid-2,4,6-tribromophenyl ester are added dropwise over the course of 5 minutes. The mixture is then reacted at room temperature for a further 15 hours. The solid is filtered off, washed with water and 11.3 parts of the reaction product are isolated. The filtrate is evaporated and the resulting solid washed with acetone, whereupon 41.7 further parts are obtained. Both portions have the same melting point of 263°–264°C and agree with the formula

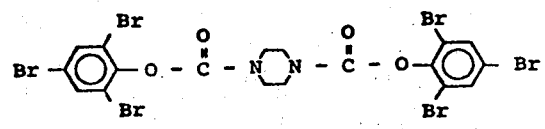

The compounds of formulae

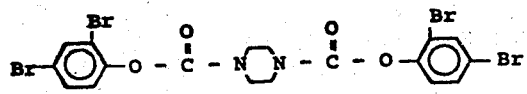

and

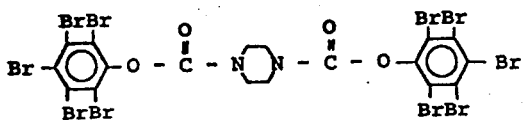

are produced in analogous manner.

EXAMPLE 2

39.35 Parts of chlorocarbonic acid-2,4,6-tribromophenyl ester are introduced into 350 parts of tetrahydrofuran. 5.8 Parts of N,N'-diethylethylene diamine together with 10.1 parts of triethylamine are added dropwise at 10°–15°C over the course of 15 minutes. The mixture is then allowed to react at room temperature over the course of 3 hours and at reflux temperature over the course of 2 hours. After filtration of the triethylamine hydrochloride and evaporation of the filtrate the resulting solid is recrystallized from carbon tetrachloride and then extracted with ethanol. White crystals having a M.P. of 169°–171°C and which are of formula

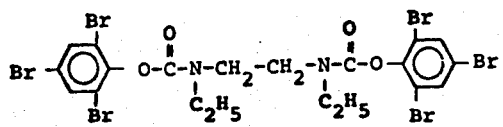

are obtained.

The compound of formula

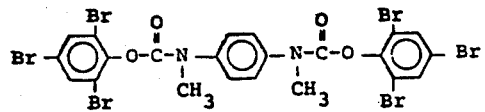

is produced in analogy with Example 2. The resulting crude product is first washed with 1000 parts of water and then with 1000 parts of acetone. White crystals, having a M.P. of 314°–316°C, are obtained.

EXAMPLE 3 (Application)

The first compound of Example 1 was mixed in an extruder at 250°C with 9 times its weight of polyethylene terephthalate which had previously been dried overnight at 110°C in a vacuum (viscosity coefficient $[\eta] = 0.5$ in m-cresol). The resulting mixture was extruded and cut to a granulate, which was predried in the same way and spun at 275°C into fibres of 120 denier.

Knit fabrics were produced from these threads on an open top circular knitting machine and burnt in double layers according to German Inflammability Test DIN 53906. The results were compared with those obtained from the same test with untreated polyethylene terephthalate.

Another burning test was effected as follows: The spun threads were wound in 6 layers around a glass rod. The glass rod was vertically fastened in a burning chamber, as used for the burning test in accordance with German Inflammability Test DIN 53906, and kindled with the ignition device over the course of 50 seconds. The time was measured in which the burning border from ignition receded by 5 cms, and this was compared with the result from the same test with untreated threads.

What is claimed is:

1. A compound, of the formula

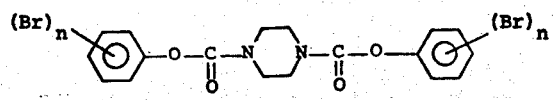

in which
each $n$, independently, is an integer 2 to 5.

2. A compound according to claim 1, of the formula,

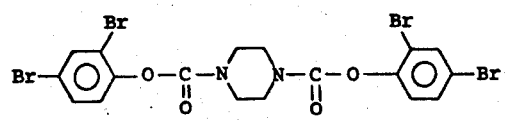

3. A compound according to claim 1, of the formula,

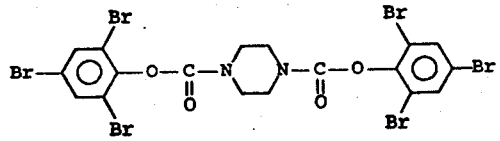

4. A compound according to claim 1, of the formula,

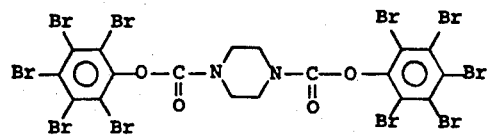

* * * * *